(12) United States Patent
Tsuru

(10) Patent No.: US 6,548,288 B2
(45) Date of Patent: Apr. 15, 2003

(54) METHOD FOR PRODUCING HIGH DENSITY ANTAGONISTIC MICROBE BASE MATERIAL AND HIGH DENSITY ANTAGONISTIC MICROBES PRODUCED BY THE SAME

(75) Inventor: Shinya Tsuru, Tokyo (JP)

(73) Assignee: Jeong Hee Choi, Kyonggi-do (KR)

( * ) Notice: Subject to any disclaimer, the term of this patent is extended or adjusted under 35 U.S.C. 154(b) by 0 days.

(21) Appl. No.: 09/969,223

(22) Filed: Oct. 2, 2001

(65) Prior Publication Data

US 2002/0119123 A1 Aug. 29, 2002

(30) Foreign Application Priority Data

Oct. 2, 2000 (KR) ............................................. 00-57911

(51) Int. Cl.⁷ .................................................. C12N 1/12
(52) U.S. Cl. ................................ 435/252.1; 435/252.4; 435/253.5; 435/253.6; 435/255.2; 435/255.21; 435/255.7
(58) Field of Search ........................... 435/252.1, 252.4, 435/253.5, 253.6, 255.2, 255.7, 255.21

(56) References Cited

U.S. PATENT DOCUMENTS

2001/0001673 A1 * 5/2001 Coppens et al.

* cited by examiner

*Primary Examiner*—Francisco Prats
*Assistant Examiner*—Susan D. Coe
(74) *Attorney, Agent, or Firm*—Marshall, Gerstein & Borun

(57) ABSTRACT

The present invention discloses high density antagonistic microbe base materials and a method of producing the same, more particularly, a method for preparing high density antagonistic microbe base material comprising the steps of: inoculating a mixture of native microbes as main components to organic medium to obtain crude bacteria by subculture; and further inoculating the obtained crude bacteria in a culture medium consisting of crushed soil from volcanic rocks mineral, combined nutrients and water, culturing and then being subjected to air ventilation under agitating the cultured material along the rise in temperature.

10 Claims, 7 Drawing Sheets

METHOD FOR PRODUCING HIGH DENSITY ANTAGONISTIC MICROBE BASE MATERIAL AND HIGH DENSITY ANTAGONISTIC MICROBES PRODUCED BY THE SAME

FIELD OF THE INVENTION

The present invention is directed high density antagonistic microbe base materials and a method of producing the same.

BACKGROUND OF THE RELATED ART

In normal soil environment, a number of microbes take charge and share such environment together, and they continuously increase with organic materials from the soil environment. In this mechanism, the microbes degrade the organic materials and progressively decompose or decay soil the nutrient drained out of degraded materials to lead to improvement of growth ability of the soil.

Growth ability of the soil, that is, richness (or fertility) of the soil often serves as a criterion to determine whether the soil is "living" or "effective" to the growth of a plant. Efficient organic and/or inorganic materials are degraded or decomposed, fused and dissolved and form polymer compounds oxidized, polymerized or shrunk by chemically or biologically reacting such materials which is called as a "decay process." It means that the soil in which such decay processes smoothly and actively performs has high fertility. By enhancing the fertility of the soil to result in the healthy and active breeding or growth of plants, it is achieved that the circumstance and natural environment to be preserved and protected; harvest capacity or yield of agricultural crops and vegetables and their qualities be increased; damages caused by insects be decreased; and interference or problems at cyclic cultivation be protected or inhibited.

Products generated by the decay process are polymeric electrolytes having acidic radicals at an external side of molecules comprising the electrolytes and are known that they function to purify the soil by means of chemical reaction accompanying with dissociation of such acidic radicals.

Such soil is formed by a combination of physical, chemical and biological activations, although it is based on the decomposition mechanism of organic materials led by microbes.

Since then industrial modernization including agricultural application, agricultural manners and/or cultivation methods by utilizing artificial fertilizers are distributed and executed in a wide application of relative art, and provision of organic materials to field and/or farmland. Furthermore, crop yield remarkably has increased by advance in agricultural techniques including multiple cultivation of single-crops and/or distribution of a variety of facilities, etc. However, the richness of soil, for instance, farmland was rapidly decreased every year and dependence to agricultural chemicals is raised so that farms crop rotation being interrupted were increased; and quality deterioration has been resulted. All of such problems were caused by ecological collapse or destroy of livings in the soil and/or lowering of multiple reactions of above described microbes.

Comparing B/F values (e.g., relative ratio of Actinomycetes to Filamentous fungi) between of healthy and ideal farmland and of multiple crops hindered farmland, the former is at least 1000 while it was less than 500 for the later case. Additionally, the larger multi-crops rotation is hindered, the higher increasing rate of filamentous fungi is. It was well known that about 80% soil damage by blight insects of crops is caused by the filamentous fungi. It was also confirmed that if the B/F value is high, yield, quality or the like are also improved. Therefore, it will be appreciated from the above states that biological activation of soil microbes serves a very important role to such crop quality or yield.

Consequently, continuous use of chemical and/or artificial fertilizers and agricultural chemicals progressively lead to collapse of the harmony of microbes; increase of multi-crops rotation hindered farmland and lowering of the richness of soil.

In addition to the above, the contamination of surrounding environment we live and the foods we eat which were induced by such chemical fertilizers and agricultural chemicals raises a question of safety to human beings. As a solution to eliminate such problem, organic cultivation takes an increasing interest. Nevertheless, the organic cultivation has an alternative problem as yet, for instance, of the contamination of underwater by acetic acid base nitrogen generated during the decomposition of organic materials due to mass introduction of un-degraded organic materials.

SUMMARY OF THE INVENTION

Accordingly, in order to solve the limitations of the related art mention above, the present invention is directed to ultra-high density microbe base materials comprising, for example, actinomycetes, filamentous fungi, bacteria and yeast or the like that have reinforced or enhanced antagonistic activity against native microbes to improve such soil environment and provides a preparation method of such ultra-high density microbe base material.

Another object of the present invention is to provide a high density antagonistic microbe base material prepared by the above described method.

Such method for preparing the high density antagonistic microbe base material comprises the following steps:

(1) to organic medium containing rice bran as a principle ingredient, a mixture of native microbes including *Streptomyces actinomycetes,* Corynebacterium bacteria, Aspergillus filamentous fungi and/or Saccharomyces yeast as main components is inoculated to obtain crude bacteria by subculture; and (2) said crude bacteria is further inoculated in a culture medium consisting of crushed soil from volcanic rocks mineral, combined nutrients and water, cultured for a desired period of time, then is subjected to air ventilation under agitating the cultured material along the rise in temperature.

Preferably, the crude bacteria in the first (1) step are under organic cultivation executed under 25 to 40% by weight of water content at 25 to 30° C. for 4 to 5 days under agitating several times per day.

Furthermore, the culture medium in the second (2) step is preferably made by adding 10 to 20 parts by weight of a combined nutrient to 100 parts by weight of a crushed soil from volcanic rocks mineral; and blending together them under controlling the water content to reach 30 to 40% by weight.

Such high density antagonistic microbe base material formed as described above is further granulated after the second step.

Preferably, such base material prepared according to the present inventive method has a controlled water content of 4 to 5% by weight. To obtain such water content, the base material is subjected to moisture evaporation and is forcibly dried in order simultaneously with said granulation step.

The high density antagonistic microbe base material is obtained by inoculating a mixture of native microbes including *Streptomyces actinomycetes,* Corynebacterium bacteria, Aspergillus filamentous fungi and Saccharomyces yeast as main components to organic medium containing rice bran as a principle ingredient to practice subculture of a crude bacteria; and further inoculating such crude bacteria in a culture medium consisting of crushed soil from volcanic rocks mineral, combined nutrients and water, culturing it for a desired period and then air-ventilating the cultured material under agitating along the rise in temperature.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention, in the drawings.

DETAILED DESCRIPTION OF THE INVENTION

Figure 1:
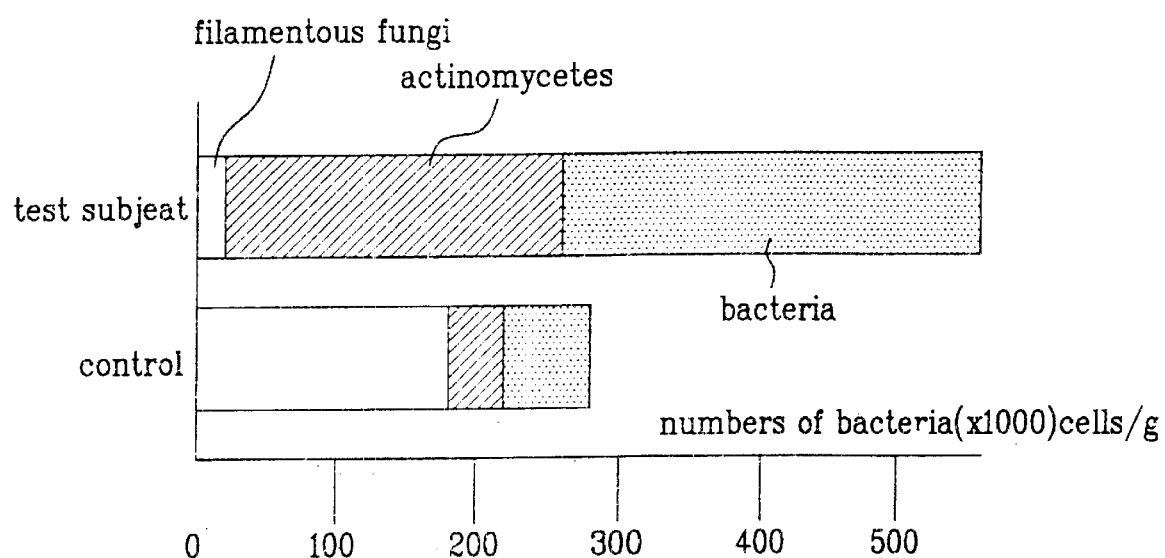
FIG. 1 illustrates a graph illustrating the recovery state of soil along with an increment/decrement in numbers of bacteria, when the high density antagonistic microbe base material according to the present invention was used in the soil in trouble.
Figure 2A:
FIG. 2 illustrates photographs indicating the inhibition of Filamentous fungi by Actinomycetes, when the high density antagonistic microbe base material according to the present invention was used; upper part (FIG. 2A) among the photographs showing the state before while the lower part (FIG. 2B) being after treating with the base material. Simple and clear white portions in the photographs are colonies of Filamentous fungi, and thin and white portions are colonies of Actinomycetes. From the lower photograph, it is noticeable that after treating the soil in a problem with the base material according to the present invention, the filamentous fungi colonies are reduced while for actinomycetes case they are increased.
Figure 2B:
Figure 3A:
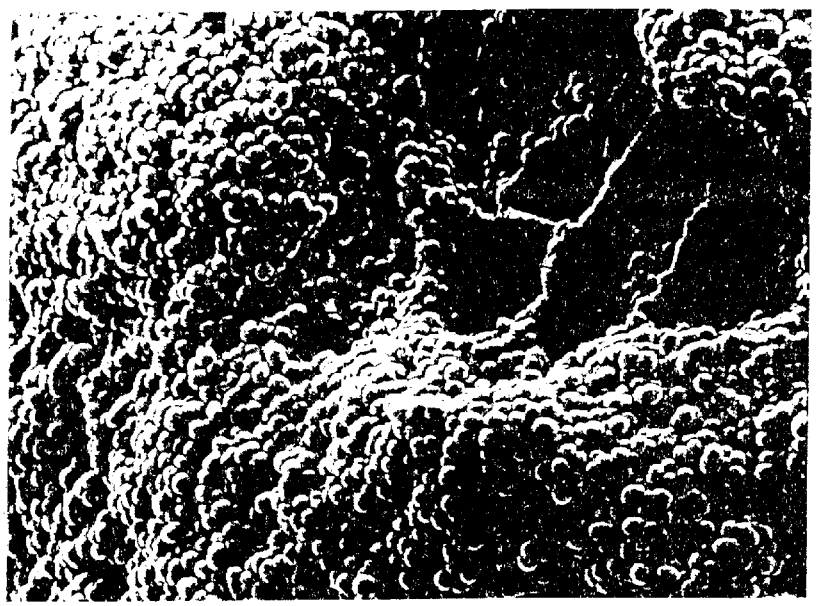
FIGS. 3 to 7 illustrate SEM photographs to represent actinomycetes contained in the high density microbe base material of the present invention by means of SEM microscopic analysis.
Figure 3B:
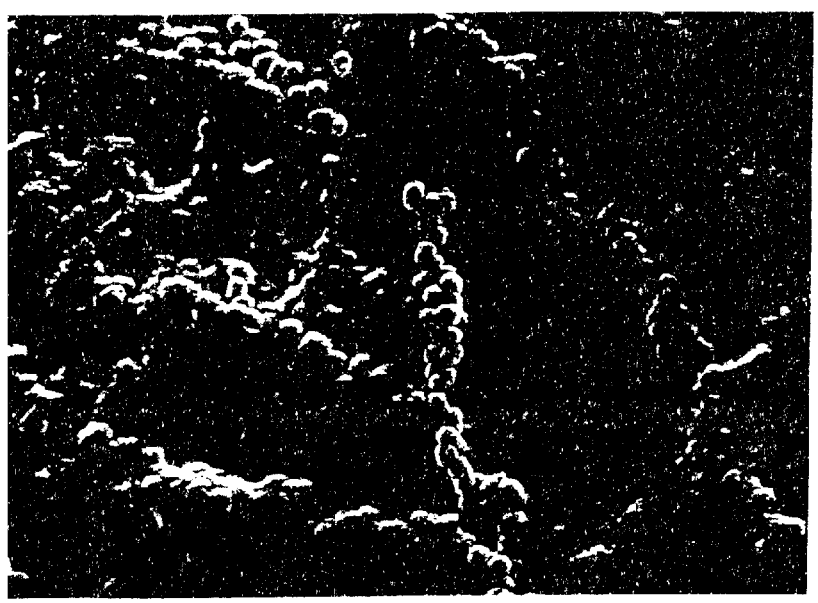
Figure 4A:
Figure 4B:
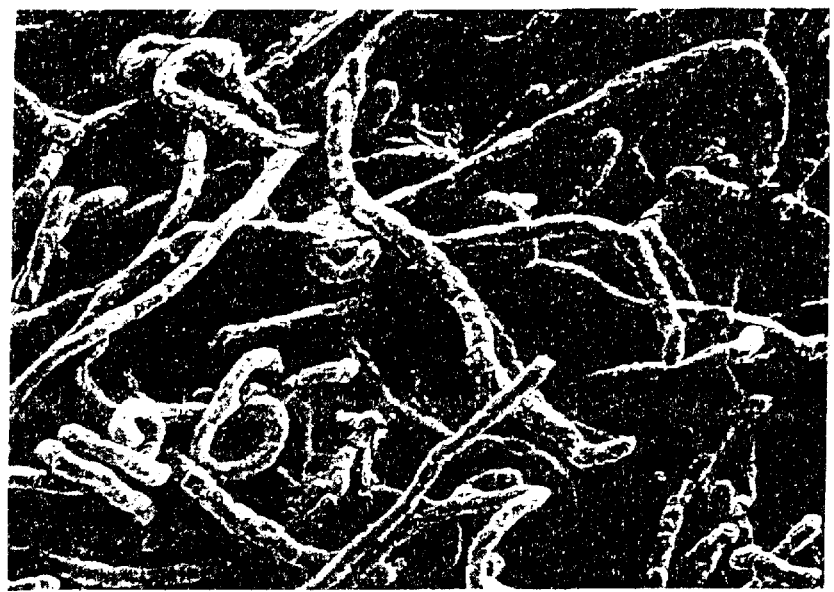
Figure 5A:
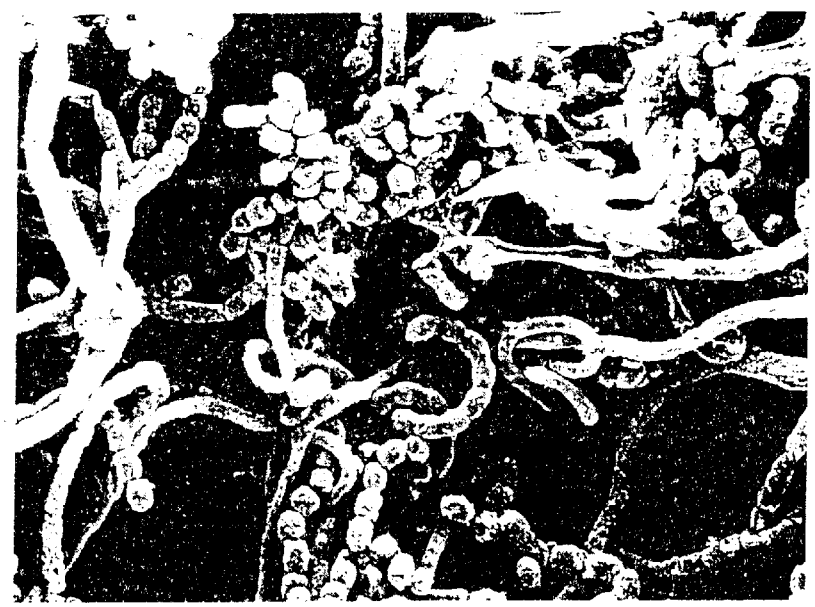
Figure 5B:
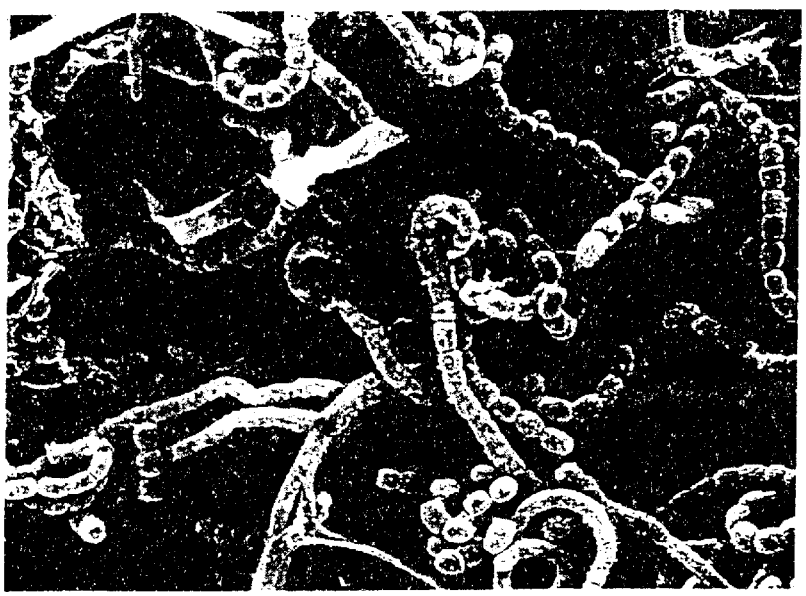
Figure 6A:
Figure 6B:
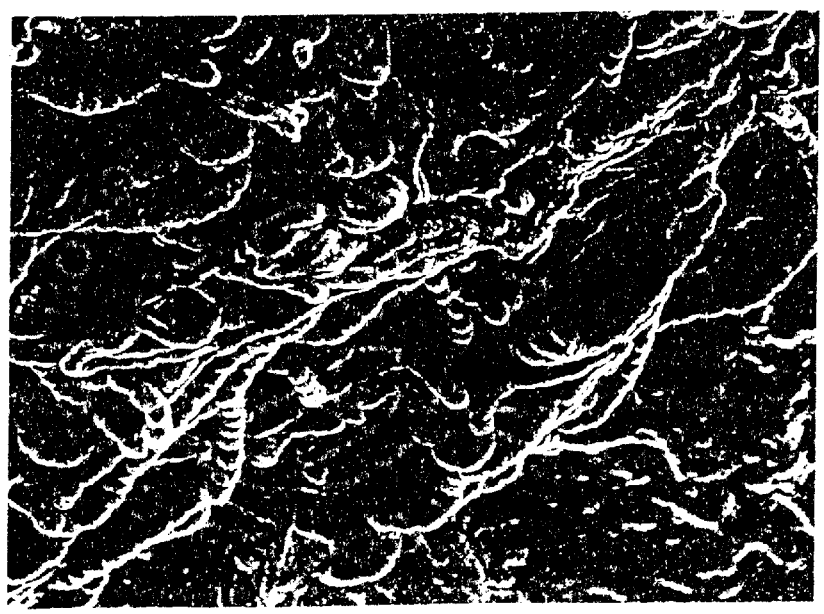
Figure 7A:
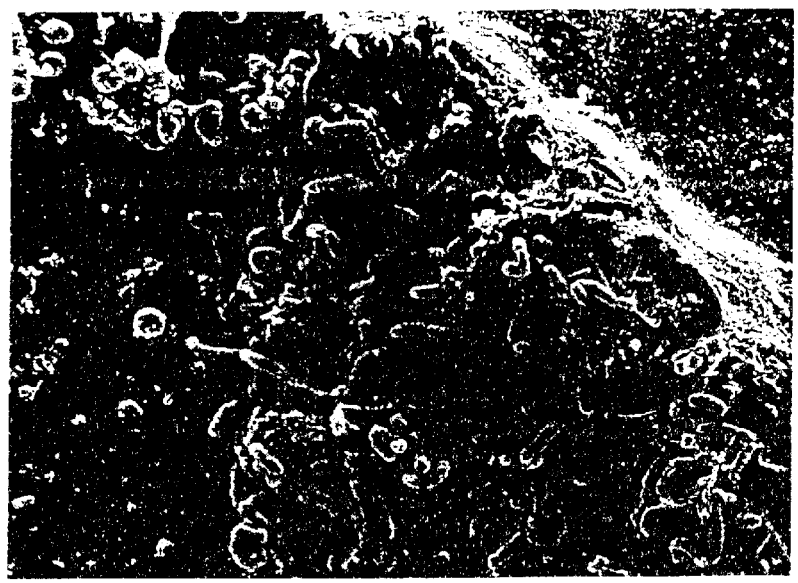
Figure 7B:

Reference will now be made in detail to the preferred embodiments of the present invention, examples of which are illustrated in the accompanying drawings.

As described above, the present invention is to provide a method for preparing the high density antagonistic microbe base material comprises the following steps of:

(1) inoculating a mixture of native microbes including *Streptomyces actinomycetes,* Corynebacterium bactera, Aspergillus filamentous fungi and Saccharomyces yeast as main components to organic medium containing rice bran as a principle ingredient to obtain crude bacteria by subculture; and (2) further inoculating the obtained crude bacteria in a culture medium consisting of crushed soil from volcanic rocks mineral, combined nutrients and water, culturing for a desired period and then being subjected to air ventilation under agitating the cultured material along the rise in temperature.

The present invention is also directed to a high density antagonistic microbe base material produced by the method described above.

Such crude bacteria is extracted from soil and selectively cultured and contains actinomycetes of Streptomyces genus, bacteria, filamentous fungi and yeast. The crude bacteria is preferably a combination of microbes from soil including actinomycetes of Streptomyces genus, bacteria of Corynebacterium genus, filamentous fungi of Aspergillus genus and yeast of Saccharomyces genus, more preferably a mixture of soil microbes such as Streptomyces-Griseus actinomycetes, Corynebacerium-Ammonigenum bacteria, Aspergillus-Versicolor filamentous fungi and Saccaromyces-Cervisiae yeast.

Such crude bacteria selectively cultured is firstly cultured in an organic culture process then subsequently cultured in a culture medium consisting of crushed soil obtained from volcanic rocks mineral containing sedimentary soil. The crude bacteria in the first culture (1) step is preferably under organic cultivation executed under 25 to 40% by weight of water content at 25 to 30° C. for 4 to 5 days under agitating several times per day.

Continuously, the culture medium in the second (2) step is preferably made by adding 10 to 20 parts by weight of a combined nutrient to 100 parts by weight of crushed soil obtained from volcanic rocks mineral; and blending together them under controlling the water content to reach 30 to 40% by weight.

The crushed soil of volcanic rock mineral used in the present invention is obtained near Handa basin near in Nagano-ken, Japan and comprises rounded conglomerates such as sandstone, clay slate or so on or andecite rock component. Other conditions including cultural nutrients and/or culture condition are in compliance with customarily used in the application of technology in connection with the present invention.

Such high density antagonistic microbe base material produced by said method is further granulated according to any typical manner and preferably has 4 to 5% by weight of water content. In order to accomplish such water content, such base material is subjected to moisture evaporation and is forcibly dried in order simultaneously with said granulation step.

With regard to the preparation method of base material according to the present invention, it has about $10^{11}$ and $10^{12}$ cells/g of the adsorption density of the antagonistic microbes to the base material, and $10^3$ to $10^4$ of B/F value ((numbers of actinomycetes+numbers of bacteria)/(numbers of filamentous fungi)). Also, it can adsorb and sustain metabolic products having high antagonistic ability in the culture process.

Thus, according to the base material produced by the present invention, it is possible to speedily prevent damages by fungi of soil, for instance, wilt including bacterial wilt and fusarium will, and Heli-cobasidium mompa.

The base material prepared according to the present invention may be used along and/or in combination with other typical organic fertilizers to scatter and/or initial manure to distribute over a wide area to be treated.

In case of introducing it into organic compound fertilizer during the production process, it can be accelerated to supply the nutrients generated by microbes to achieve improvements of continuation and an immediate effect of the fertilizer and to apply the fertilizer as an additional manure.

The amount to be used may be determined in consideration of soil type and nature or conditions of crops. In case of scattering it over all of the area to be treated, it can be typically 20 to 30 kg/10 a.

On the other hand, when it is used in ridging to breed saplings, it amounts about 10 to 15 kg per 1m3 while, for charging it into ports, it depends on crops to breed.

Additionally, in case of executing fermentation of organic materials such as compost or farmyard manure, it is generally 10 to 15 kg/t. However, it must be avoided to combine the base material of the present invention with any bactericides or fungicides.

Typical amounts to be used and methods of use are described in the Table 1 below:

TABLE 1

| | Subject to treat | Amount to apply | | Method of use |
|---|---|---|---|---|
| Greens, Fruits, & flowers | Breeding sapling | 1 m³ of ridging to breed sapling | 10–15 kg | Blending at breeding or preparing ridge soil with the base material of the present invention |
| | Before planting | 10a | 20–30 kg | Cultivating at initial manuring together with compost or organic compound fertilizer. For dried soil, irrigating the land. |
| | During growth | 1 plant | 10–50 g | Digging a ditch and spraying the base material over the patch or field then covering it. |
| | | Used as additional manure | 20 kg/10a | Mixing with organic fertilizer, spraying over field and lightly watering it. |
| | Growing in pot for cultivation of flowers | Adding to ridge soil, 1 ton | 10–15 kg | Blending the base material with ridge soil Before planting it into pot. |
| | As used in aqueous solution (1) spraying on surface of leafs | 5 kg Diluted in 500 liter water by 100 times | 1–2 times per month, spraying | Avoiding the blending of the base material with agricultural chemicals, although it can be mixed with other liquid fertilizer. |
| | (2) water culture | Diluted By 2000–3000 times and provided into solution tank | | |
| Fruit Trees | Infant trees (transplant) | 1 tree | 1–2 kg | Blending equal amount of organic fertilizer and the base material and scattering the mixture into plant hole and covering it, repeatedly. |
| | 5–10 years old trees | 1 tree | 2–3 kg | Digging around the tree, and mixing equal amounts of the organic fertilizer and the base material and scattering it into the hole and covering it, repeatedly. |
| | 20 years or above | 1 tree | 5 kg | Digging around the tree, mixing equal amounts of the organic material and the base material, scattering it into the hole and covering it, repeatedly. For dried soil, watering it at the same time. |
| Green | At preparing the Green | 1 m² | 1–2 kg | Blending the organic material and the base material, and adding the mixture to planting soil and watering it. |
| | For green | 1 m² | 50 g | Driving the mixture of wooden soil, organic material and the base material into planting hole during aeration process. |
| | For fairway | 1 m² | 50 g | combining the base material with organic material then scattering the mixture by 1 kg per 1 m² of the area and watering it. |
| manure | | 1 ton | 2–3 kg | Mixing the base material in 2–3 kg with 20 kg of rice bran, fermenting then adding it into compost. The compost controlled water content of the compost to 50% |

The present invention will be described in more detail by way of Examples, which should not be construed as limiting the invention thereto.

EXAMPLE 1

Subculture of Crude Bacteria

To an organic medium containing rice bran as a principle ingredient, a mixture of native microbes including Streptomyces-Griseus actinomycetes, Corynebacterium-Ammonigenum bacteria, Aspergillus-Versicolor filamentous fungi and Saccharomyces-Cervisiae yeast as main components is inoculated to obtain crude bacteria by subculture. Such subculture of crude bacteria is executed under the desired conditions which can be defined and/or controlled in a laboratory level by the generally known manners in the application in association with the present invention.

Genus and numbers of the crude bacteria (that is, a mixture of soil microbes) exerted by subculture were determined after culturing such bacteria on albumin agar culture medium and Rosebengal agar culture medium. As the results of microscopic observation and countering by pour agar plate method, the principle nomenclature of such crude bacteria and the numbers of the bacteria are found as showns in Table 2 below:

TABLE 2

Nature of crude bacteria and numbers thereof (Cells/g)

| Nature of crude bacteria | Level of bacteria numbers | Medium | Culture |
|---|---|---|---|
| Filamentous fungi: F | $10^7$–$10^8$ | Rosebengal | 3 days, 25° C. |
| Yeast: Y | $10^8$–$10^9$ | | |
| Actinomycetes: A | $10^8$–$10^9$ | Albumin | 6 days, 28° C. |
| Bacteria: B | $10^8$–$10^9$ | | |

As a result of measuring the numbers of bacteria, it is understood that about $10^7$ to $10^8$ of Filamentous fungi, about $10^8$ to $10^9$ of Yeast, $10^8$ to $10^9$ of Actinomycetes and about $10^8$ to $10^9$ of Bacteria were existed in the soil mixture.

EXAMPLE 2

Secondary Culture of Crude Bacteria

The above firstly cultured crude bacteria was further cultured by inoculating said crude bacteria in an alternative culture medium consisting of crushed soil from volcanic rocks mineral, combined nutrients and water and culturing for a desired period of time.

The crushed soil containing sedimentary soil was obtained near Handa basin area in Nagano-ken, Japan, which included rounded conglomerates such as sandstone, clay slate or so on or andecite rock component. The analysis result of the crushed soil from volcanic rock minerals executed by the Japan fertilizer authorization foundation is shown in the following Table 3:

TABLE 3

| Ingredient | Content |
|---|---|
| $P_2O_5$ | 312.2 mg |
| N | 15.4 mg |
| $SiO_2$ | 55.80% |

TABLE 3-continued

| Ingredient | Content |
|---|---|
| $Al_2O_3$ | 20.19% |
| CaO | 4.13% |
| MgO | 1.81% |
| $K_2O$ | 1.40% |
| $H_2O$ | 1.84% |
| Ignition loss | 2.75% |

It will be appropriated that the present invention can use the crushed soil exerted from other area, not limited to Handa basin area if it contains all of ingredients and composition thereof equal to that described in the above Table 3. Also, said soil further comprises other actinomycetes or bacteria in the natural state typically existing in soil.

To 100 kg of such crushed soil having the composition cited in Table 3, 2 kg of kanigara powder, 5 kg of rice bran and 5 kg of morocone powder were introduced in combination and added with water to thereby form a medium having 25% of water content. The medium was inoculated by such previously cultured soil microbes, then was subject to a secondary culture of such microbes at 28 to 30° C. In order to accelerate the fermentation process, the secondary culture was executed by means of heater utill the temperature of such medium was reached to 30° C. Since it is difficult to determine the culture conditions during the culture process in case of the separate culture manner, the increase graph of the cultured material was made on the basis of the time consumed and the alteration of the temperature.

When the culture process progresses from the induction period to the culture increasing period, the temperature of medium sharply increased.

By air-ventilating the cultured material under agitating after passing the normal state period and immediately before entering into the destruction period, it was accomplished to protect it from overheating. Simultaneously, air supplying and removal of gas generated could be carried out to thereby the produced material to be uniformly distributed.

Furthermore, both of agitation and sieving processes can be executed at the same time.

Such cultured material is preferably granulated to allow the air ventilation of cultured material to be successively practiced even its depth and to increase the concentration of bacteria. Additionally, it is possible to obtain cells and/or spores increased by such method described above.

Such operation was performed 2 to 3 times per day, provided that graphs of time was elapsed and temperature alteration was monitored and controlled to reach the peak point of 55° C.

After completing the culture process, the produced material was cultured on albumin agar culture medium in order to counter the numbers of bacteria based on genus of such bacteria. The counting means was the pour agar plate method to result in the following Table 4:

TABLE 4

Nature of crude bacteria and numbers thereof (Cells/g)

| Nature of crude bacteria | Level of bacteria numbers | Medium | Culture |
|---|---|---|---|
| Filamentous fungi: F | $10^8$–$10^9$ | Rosebengal | 3 days, 25° C. |
| Yeast: Y | $10^6$–$10^7$ | | |

TABLE 4-continued

Nature of crude bacteria and numbers thereof (Cells/g)

| Nature of crude bacteria | Level of bacteria numbers | Medium | Culture |
|---|---|---|---|
| Actinomycetes: A | $10^{12}$–$10^{13}$ | Albumin | |
| Bacteria: B | $10^{12}$–$10^{13}$ | | 6 days, 28° C. |
| B/F value | $10^{3}$–$10^{4}$ | | |

From the above described result, it is understood that actinomycetes and bacteria noticeably increase compared with the other two materials, that is, filamentous fungi and yeast.

EXAMPLE 3

Drying of Cultured Material

Such cultured material produced by Example 2 is water-evaporated in order for 3 to 4 days; then controlled to have 4 to 5% by weight of final water content by forced drying operation and sealed into a high sealing bag, to thereby permit the storage of microbes in a resting state at ambient temperature.

Therefore, it is possible to continuously produce the microbe base material of the present invention in a stable state and, in turn, to supply the material with no alteration and/or degradation thereof from the viewpoint of distribution stability and preservation.

EXAMPLE 4

Separation of Strain Colonies and Identification Thereof.

In order to separate and purify the representative strain colonies and examine their conditions, performed at the slide culture operation to portably carry and monitor them through a microscope to determine genus of the observed strain colonies. The results observed are shown in Tables 5 to 8 below:

TABLE 5 fungi
Nature of colonies

| Strain | Size (mm) | shape | Type of hypha | Color | Determination by observing through microscope |
|---|---|---|---|---|---|
| 1 | 30 × 30 | Round | Linear | White | Mucor |
| 2 | 11 × 11 | " | Flat | Dark green | Aspergillus |
| 3 | 8 × 8 | " | Linear | " | Mucor |
| 4 | 11 × 11 | " | Flat | " | Aspergillus |
| 5 | 20 × 20 | " | Linear | " | " |
| 6 | 15 × 15 | " | Linear | " | " |
| 7 | 10 × 10 | " | Flat | " | " |
| 8 | 12 × 12 | " | Flat | " | " |
| 9 | 10 × 10 | " | Flat | " | " |
| 10 | 5 × 5 | " | Flat | Yellow green | " |

TABLE 6 yeast
Nature of colonies

| Strain | Size (mm) | shape | Color | Uplift | Margination | Other | Determination by observing through microscope |
|---|---|---|---|---|---|---|---|
| 1 | 4 × 4 | Round | White | Convex shape | Erose | Surface phase | Saccharomvces |
| 2 | 3 × 3 | " | " | Convex shape | " | Surface phase | " |
| 3 | 3 × 3 | Star type | " | Convex shape | " | Surface phase | " |
| 4 | 4 × 4 | round | " | Convex shape | " | | " |
| 5 | 2.5 × 2.5 | " | " | Convex shape | " | Surface phase | " |
| 6 | 2 × 2 | " | " | Convex shape | " | Surface phase | " |
| 7 | 2 × 2 | " | Tint white | Convex shape | entire margine | | " |
| 8 | 1.5 × 1.5 | " | White | Convex shape | entire margins | | " |
| 9 | 3.5 × 3.5 | Star type | " | Convex shape | Erose | Surface phase | " |
| 10 | 3.5 × 3.5 | round | " | Convex shape | " | Surface phase | " |

TABLE 7 actinomycetes
Nature of colonies

| Strain | Size (mm) | shape | Color | Uplift | Margination | Determination by observing through microscope |
|---|---|---|---|---|---|---|
| 1 | 9 × 9 | Round | Greenish gray | flat | Thread type | Streptomyces |
| 2 | 9 × 9 | " | " | " | " | " |
| 3 | 9 × 9 | " | " | " | " | " |
| 4 | 5 × 5 | " | Dark yellow | " | " | " |
| 5 | 9 × 9 | " | Greenish | " | " | " |
| 6 | 8 × 8 | " | Gray white | " | " | " |
| 7 | 9 × 9 | " | Greenish gray | " | entire margin | " |
| 8 | 8 × 8 | " | " | " | " | " |
| 9 | 8 × 8 | " | " | " | Erose Surface phase | " |
| 10 | 7 × 7 | " | Yellow white | " | Erose Surface phase | " |

TABLE 8 actinomycetes

| | Nature of colony | | | | | Nature of cell | | | | | | |
|---|---|---|---|---|---|---|---|---|---|---|---|---|
| Strain | Size (mm) | shape | Color | margin | Spawn | Gram stain | Type | Mobility | Catalase | orgindaze | O.F. test | Determination |
| 1 | 1.0 × 1.0 | g. round | White | entire | − | + | Short stick | − | + | + | 0 | C |
| 2 | 0.5 × 0.5 | " | Yellow | " | − | + | " | − | (+) | + | 0 | C |
| 3 | 0.5 × 1.0 | Oval | Yellowish white | " | − | + | Sphere | − | + | + | F | S |
| 4 | 1.0 × 2.0 | " | Yellowish white | " | − | + | " | − | − | + | 0 | M |
| 5 | 1.5 × 1.5 | Round | White | " | − | + | Short stick | − | (+) | + | 0 | C |
| 6 | 0.5 × 0.7 | Oval | Yellow | " | − | − | " | − | + | + | 0 | C |
| 7 | 0.5 × 0.7 | " | Orange | " | − | − | " | − | + | + | 0 | C |
| 8 | 1.5 × 1.5 | Round | White | Entire | − | + | " | − | + | + | 0 | C |
| 9 | 1.0 × 1.5 | Oval | Yellow | " | − | + | " | − | + | + | 0 | C |
| 10 | 0.5 × 0.5 | round | white | " | − | − | " | − | + | + | F | e |

[60] *C = Corynebacterium,
S = Staphyrococcus,
[61] M = Micrococcus
E = Enterobacteriaceal The high density microbe base material according to the present invention was used in different farms to determine the effect thereof. Consequently, the results are as follows:

EXPERIMENTAL EXAMPLE 1

The result of Cucumber cultivation test by using the microbe base material of the present invention in AEWON ken.

The test was practically executed under the following conditions:

| 1. Cultivation method: | Greenhouse cultivation |
| 2. Area of greenhouse: | 14.4 m × 190.8 m = 2,747.5 m² (832.58 pyong) |
| 3. Control: | South greenhouse |
| 4. Test: | North greenhouse |
| 5. Variety of cucumber: | sharp 1 |
| 6. Experimental method | |

In the test greenhouse, a mixture comprising 10 kg of the high density antagonist microbe base material according to the present invention, 40 kg of powdered bones and 20 kg of synthesized chemical fertilizer was driven into the ground in a 55 cm depth by 2 m space by means of soil irrigator before planting the subject vegetables.

As a result, numbers of the test vegetables were increased by 20% per pyong (9.9 m²) of area compared with the control and, even after completing the harvest of the control vegetables, it was found that the test vegetables can be gathered for about one month more.

EXPERIMENTAL EXAMPLE 2

The result of Spinach cultivation test by using the microbe base material of the present invention at greenhouse farm in HANDA-shi, NAGANO ken.

The test was practically executed under the following conditions:

1. Variety of spinach: native species
2. Experimental method

The high density antagonist microbe base material according to the present invention was mixed with 1.8 liter of rice bran in an amount of 1 kg per pyong of area; then scattered and cultivated.

As a result, it was found that the test spinach treated by the base material of the present invention was the product with increased numbers of roots while having short length of roots. Also, the produced spinach contained frequent amount of chlorophylls; was heavier per head; and was harvested in the improved yield more than of the control. On the contrary, the untreated control by the base material according to the present invention was found that it had roots longer and thinner, reduced number of roots and amount of chlorophylls less than of the treated products; although it has one more leaf than the treated product, it was lighter per head and harvested in a reduced yield. The test results are shown in the following Table 9:

TABLE 9

Test result in the spinach farm

|  | Test subject | Control |
|---|---|---|
| Weight of 1 head | 51.0 g | 35.0 g |
| Length of first leaf | 26.5 cm | 27.0 cm |
| Length of root | 13.0 cm | 18.0 cm |
| Numbers of leaf | 11.0 | 12.0 |
|  | Chlorophylls | Chlorophylls |
| Primary leaf 1 | 30.8 | 24.3 |
| 2 | 28.0 | 26.5 |
| 3 | 36.8 | 34.3 |
| 4 | 31.1 | 33.7 |
| 5 | 46.0 | 43.8 |
| 6 | 46.0 | 29.4 |
| 7 | 45.1 | 42.8 |
| 8 | 38.6 | 40.9 |
| 9 | 56.8 | 39.2 |
| 10 | 47.8 | 44.7 |
| 11 | 51.0 | 45.2 |
| 12 |  | 39.7 |
| means | 41.6 | 36.8 |

EXPERIMENTAL EXAMPLE 3

The result of water supply manner breeding seedlings test by using the microbe base material of the present invention in HANDA-shi, NAGANO ken The test was practically executed under the following conditions:
1. Variety of seedlings: native species
2. Breeding method: breeding in pot
3. Experimental method 1 kg of the high density antagonist microbe base material was placed in 50 liters of water, agitated under the presence of oxygen at 30° C. then scattered over the breeding plate. After 5 days, the grown saplings were transplanted in 10a.

The result showed that the saplings treated by the base material according the present invention had 10 cm of length per head and 25.8 as a mean content of chlorophylls, 5 days after transplantation. In contrast to the above result, untreated saplings were found to have 6 cm of length and 22.3 of the chlorophylls.

EXPERIMENTAL EXAMPLE 4

The result of fairway green test by using the microbe base material of the present invention in south area of NAGANO ken.

The test was practically executed for Large patch (Rhizoctonia.SP) of the fairway green in south area of NAGANO ken by treating it with the high density antagonist microbe base material.

The base material was scattered over the area in trouble of damage by soil insects by means of Cyclotron equipment in an amount of 50 g/m$^2$ (that is, 2 kg of the material per 40 m$^2$ of area).

As a result, neither damage by soil insects and/or bacteria nor harmful effect caused by mass scattering of the present inventive base material were found out in the treated area.

EXPERIMENTAL EXAMPLE 5

The result of raising outdoor test for Southern Blight disease by using the microbe base material of the present invention in HANDA-shi, NAGANO ken The test was practically executed under the following conditions:
1. Raising method: raising outdoors
2. Variety: spring onion (Allium fistulosum)
3. Test area: 330 pyong
4. Amounts of base material used: 20 kg/330 pyong
5. Experimental method 20 kg of the high density antagonist base material was mixed with other components such as sesame dregs, powdered fish, powdered bones, rice bran and chemical fertilizer to form a 500 kg self-prepared organic compound fertilizer. As the compost, 10 ton of the self-prepared manure (fermented by the base material according to the present invention) and 100 kg of commercial organic fertilizer (7-6-2) were added to 150 kg of the above self-prepared fertilizer. The combined fertilizer was scattered over the area to be further under cultivation process.

After the treatment, the area was under additional manuring for 3 times by 45 days with 110 kg, 100 kg and 50 kg of the self-prepared fertilizer, respectively.

The result showed that the induction of the Southern blight disease was sharply reduced even it had a great amount of rainfall and rained near the harvesting season; and ensured about 97% of shipping rate of vegetables.

In addition to the above, it was found that the weight of one head increased 20% than last year and for its quality, sugar content of 14.2 L class product reached about 80%.

As illustrated above, the high density antagonist microbe base material according to the present invention has advantages of imparting harmony between different microbes in soil and recovering performance and healthy environments of soil. The base material also serves to accelerate the formation of nutrient from organic materials and to prevent contamination of rivers and/or lakes.

Furthermore, it is expected that when the base material is employed in the waste of livestock industry, it can remarkably reduce the bad odor and allow the product to be utilized as a manure and/or compost including night-soil.

The forgoing embodiments are merely exemplary and are not to be construed as limiting the present invention.

The description of the present invention is intended to be illustrative, and not to limit the scope of the claims. Many alternatives, modifications, and variations will be apparent to those skilled in the art.

What is claimed is:

1. A method for preparing an agriculture growth material comprising the steps of:
   (1) inoculating an organic medium comprising rice bran with microbes including actinomycetes of Streptomyces genus, bacteria of Corynebacterium genus, filamentous fungi of Aspergillus genus, and yeast of Saccharomyces genus;
   (2) culturing the inoculated organic medium to obtain a microbe enriched medium;
   (3) inoculating a soil medium comprising soil, nutrients, and water with the microbe enriched medium; and growth material, wherein the culturing step comprises aeration and agitation to cool the inoculated soil medium.

2. The method of claim 1, wherein the organic medium comprises 25 to 40% water by weight, and wherein said organic medium is cultured according to step (2) at 25 to 30° C. for 4 to 5 days with agitation.

3. The method of claim 1, wherein the soil of step (3) comprises crushed volcanic rock.

4. The method of claim 1, wherein the soil of step (3) comprises $P_2O_5$, N, $SiO_2$, $Al_2O_3$, CaO, MgO, $K_2O$, and $H_2O$.

5. The method of claim 1, wherein the soil medium of step (3) comprises 10 to 20 parts by weight of nutrients and 100 parts by weight of soil derived from volcanic rock, and further comprises 30 to 40% by weight of water.

6. The method of claim 1, further comprising a step of granulating the agricultural growth material after the culturing step (4).

7. The method of claim 6, further comprising drying the agricultural growth material to 4 to 5% by weight of water during the granulating step.

8. The method of claim 1, further comprising a step of sealing the agriculture growth material in a container capable of retaining moisture and preserving the microbes.

9. An agriculture growth material prepared according to the method of claim 1.

10. An agriculture growth material prepared according to the method of claim 6.

* * * * *

UNITED STATES PATENT AND TRADEMARK OFFICE
CERTIFICATE OF CORRECTION

PATENT NO. : 6,548,288 B2
DATED : April 15, 2003
INVENTOR(S) : Tsuru

It is certified that error appears in the above-identified patent and that said Letters Patent is hereby corrected as shown below:

Column 14,
Lines 56-58, delete "growth material, wherein the culturing step comprises aeration and agitation to cool the inoculated soil medium." and insert -- (4) culturing the inoculated soil medium to produce an agricultural growth material, wherein the culturing step comprises aeration and agitation to cool the inoculated soil medium. -- in its place.

Signed and Sealed this

Thirtieth Day of December, 2003

JAMES E. ROGAN
*Director of the United States Patent and Trademark Office*